United States Patent
Song et al.

(10) Patent No.: US 7,273,518 B2
(45) Date of Patent: Sep. 25, 2007

(54) GAS CHROMATOGRAPH SYSTEM INCLUDING AN IMPROVED INLET SEALING MECHANISM

(75) Inventors: Wei-Liang Song, Loveland, CO (US); Lee Xu, Loveland, CO (US); Guo-Chen He, Loveland, CO (US)

(73) Assignee: Agilent Technologies Inc., Santa Clara, CA (US)

( * ) Notice: Subject to any disclaimer, the term of this patent is extended or adjusted under 35 U.S.C. 154(b) by 296 days.

(21) Appl. No.: 11/040,150

(22) Filed: Jan. 20, 2005

(65) Prior Publication Data

US 2006/0065122 A1 Mar. 30, 2006

(30) Foreign Application Priority Data

Sep. 30, 2004 (CN) .................. 2004 1 0080299

(51) Int. Cl.
*B01D 53/02* (2006.01)
(52) U.S. Cl. ............... 96/105; 96/106; 95/89
(58) Field of Classification Search ......... 96/101–107; 95/82–89; 73/23.35–23.42; 285/401, 402; 210/656, 198.2
See application file for complete search history.

(56) References Cited

U.S. PATENT DOCUMENTS 2,818,279 A * 12/1957 Knapp .................. 285/89
4,116,836 A * 9/1978 DeAngelis ............... 210/198.2
4,611,662 A * 9/1986 Harrington ................. 166/339
6,497,435 B1 * 12/2002 Luft et al. .................. 285/360
2005/0074367 A1 4/2005 O'Neil

FOREIGN PATENT DOCUMENTS

| CH | 621856 A5 | 10/1977 |
|---|---|---|
| GB | 276108 A | 6/1926 |
| GB | 795681 A | 8/1956 |
| GB | 1109759 A | 11/1966 |
| GB | 1555261 A | 6/1976 |

* cited by examiner

*Primary Examiner*—Duane Smith
*Assistant Examiner*—Robert A Clemente

(57) ABSTRACT

An inlet includes a bottom assembly and a top assembly. The bottom assembly includes at least one male unit, and the top assembly has at least one beveled surface and includes at least one female unit and a lateral driving unit. The top assembly is placed inside the bottom assembly by aligning the female unit of the top assembly with the male unit of the bottom assembly. The lateral driving unit laterally drives the top assembly and causes the beveled surface of the top assembly to rise against the male unit of the bottom assembly, allowing the top assembly to seal with the bottom assembly.

10 Claims, 5 Drawing Sheets

GAS CHROMATOGRAPH SYSTEM INCLUDING AN IMPROVED INLET SEALING MECHANISM

BACKGROUND OF THE INVENTION

As an important unit of a gas chromatograph system, an inlet is used typically for introducing liquid samples to be analyzed into the gas chromatograph system for vaporization. The vaporized samples are then pushed into a column for analysis. FIG. 1 illustrates the structure of a conventional inlet 1 of a gas chromatograph (GC) system. As can be seen from FIG. 1, the inlet 1 includes a top assembly 7, a shell unit 8, and a liner 9. The liner 9 is typically made of quartz, which can be damaged if not handled properly. Two tubes 70 and 70' are connected to the top assembly 7 for carrier gas flow and purge gas flow, respectively. The liner 9 is used for vaporizing the sample to be analyzed and is placed inside the shell unit 8. The top portion 90 of the liner 9 is covered by the top assembly 7. Threads 80 are provided on the outer surface of the top portion of the shell unit 8 for engaging with the threads (not shown) on the bottom portion of the top assembly 7. This allows the top assembly 7 to be tightly fastened to compress a sealing rubber O-ring 81 on the liner 9 so as to achieve the effect of preventing the carrier gas and the vaporized sample from leaking out of the system.

Because the samples typically cannot be vaporized completely or be cleaned completely by the carrier gas during operation of the GC system, residue of the samples may remain in the liner 9. This means that the liner 9 needs to be replaced periodically for the sake of accuracy. During replacement, it is necessary to loosen the top assembly 7 from the shell unit 8 first so as to remove the used liner 9. The top assembly 7 is then fastened to the shell unit 8 again once a new liner 9 is placed therein.

Disadvantages are associated with this prior art inlet structure. Firstly, since the sample needs to be vaporized, all parts of the inlet need to be maintained at relatively very high temperatures. Therefore, the user or operator of the GC system will have to get in contact with those high temperature components physically during the replacement operation of the liner. Secondly, the tubes connected to the top assembly restrict the movement of the top assembly and make the thread engagement of the top assembly with the shell unit very difficult. However, if the threads are not engaged correctly and are forced to mate, not only the threads will be damaged, but also the top portion of the liner will be crashed and broken due to the uneven thread engagement.

Because of the above-mentioned disadvantages, there is a need for an improved inlet structure so as to make the replacement operation both simple and user-friendly, and to minimize the possibility of damaging the inlet during the replacement operation of the liner.

SUMMARY OF THE INVENTION

An inlet includes a bottom assembly and a top assembly. The bottom assembly includes at least one male unit, and the top assembly has at least one beveled surface and includes at least one female unit and a lateral driving unit. The top assembly is placed inside the bottom assembly by aligning the female unit of the top assembly with the male unit of the bottom assembly. The lateral driving unit laterally drives the top assembly and causes the beveled surface of the top assembly to rise against the male unit of the bottom assembly, allowing the top assembly to seal with the bottom assembly.

BRIEF DESCRIPTIONS OF THE DRAWINGS

DETAILED DESCRIPTIONS OF THE PREFERRED EMBODIMENTS

Figure 1:
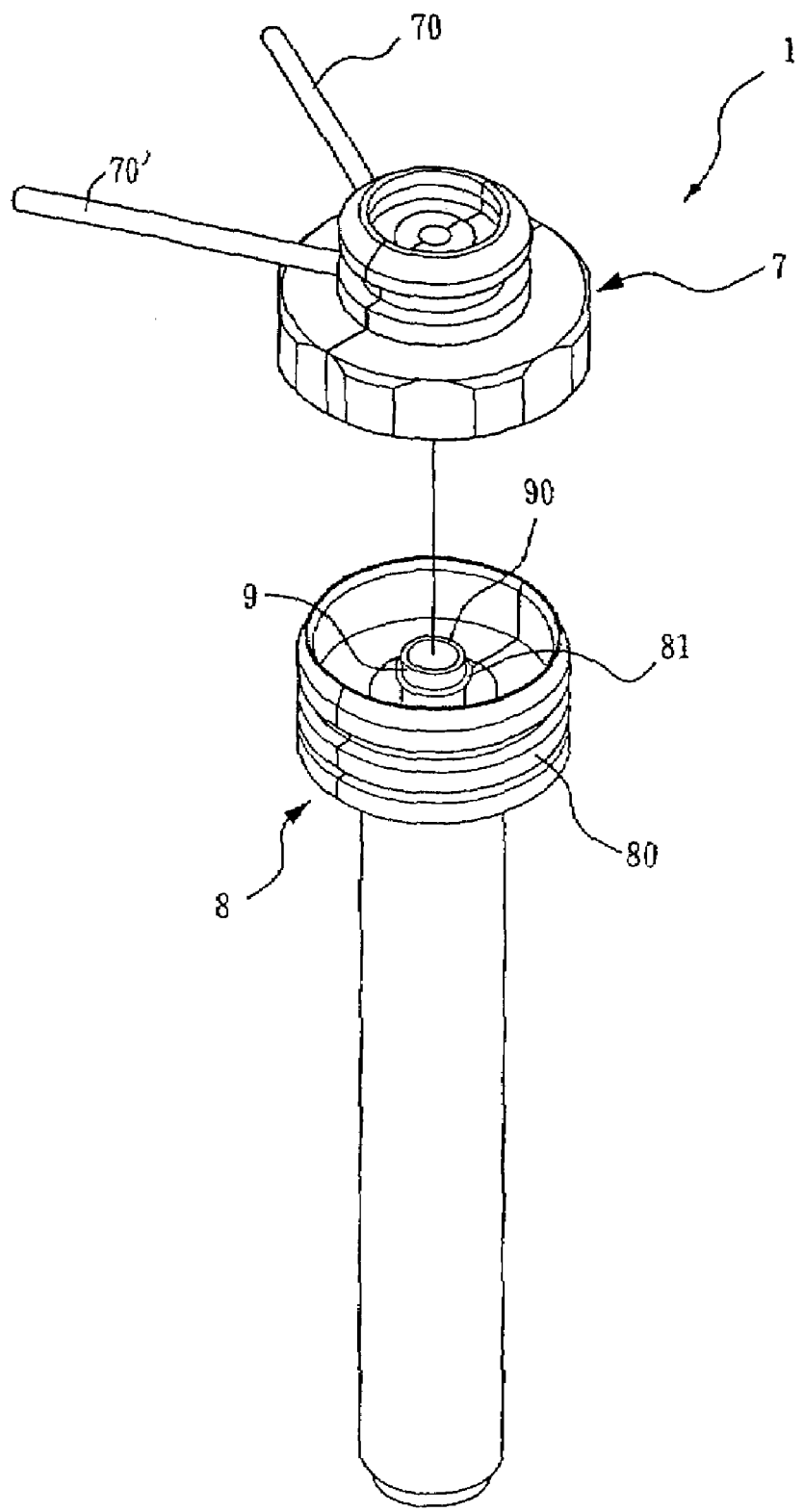
FIG. 1 illustrates the structure of a conventional inlet for a gas chromatograph system.
Figure 2:
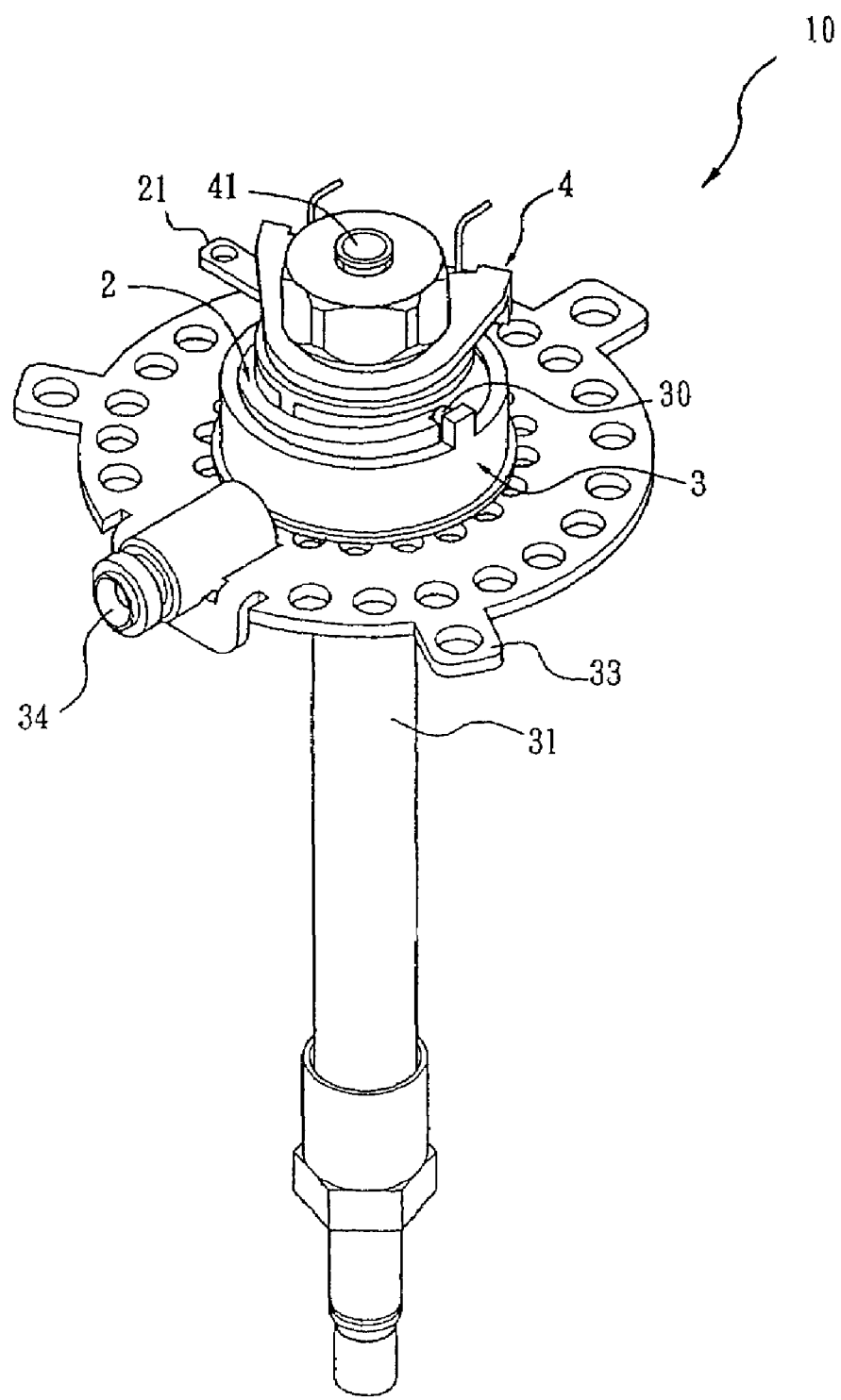
FIG. 2 illustrates a perspective view of the structure of an inlet in accordance with one embodiment of the present invention.

FIG. 2 illustrates a perspective view of the structure of an inlet 10 in accordance with one embodiment of the present invention. As can be seen from FIG. 2, the inlet 10 includes a top assembly 2, a bottom assembly 3, and a gas flow unit 4. The gas flow unit 4 is assembled on the top assembly 2. In accordance with one embodiment of the present invention, the bottom assembly 3 includes at least one male unit (e.g., 30) and the top assembly 2 includes at least one female unit (e.g., 20 and/or 20' in FIG. 3) and a lateral driving unit 21. The top assembly 2 also includes at least one beveled surface (e.g., the surfaces 23 and 23' in FIG. 3). As shown in FIG. 2, the top assembly 2 is placed inside the bottom assembly 3, but is not yet fully sealed with the bottom assembly 3. This is done by aligning the female unit of the top assembly 2 with the male unit of the bottom assembly 3. For sealing the top assembly 2 with the bottom assembly 3, the lateral driving unit 21 laterally drives the top assembly 2, causing the beveled surface (e.g., 23) of the top assembly 2 to rise against the male unit (e.g., 30) such that the top assembly 2 is sealed with the bottom assembly 3. This will be further described below, also in conjunction with FIGS. 3-6.

Figure 3:
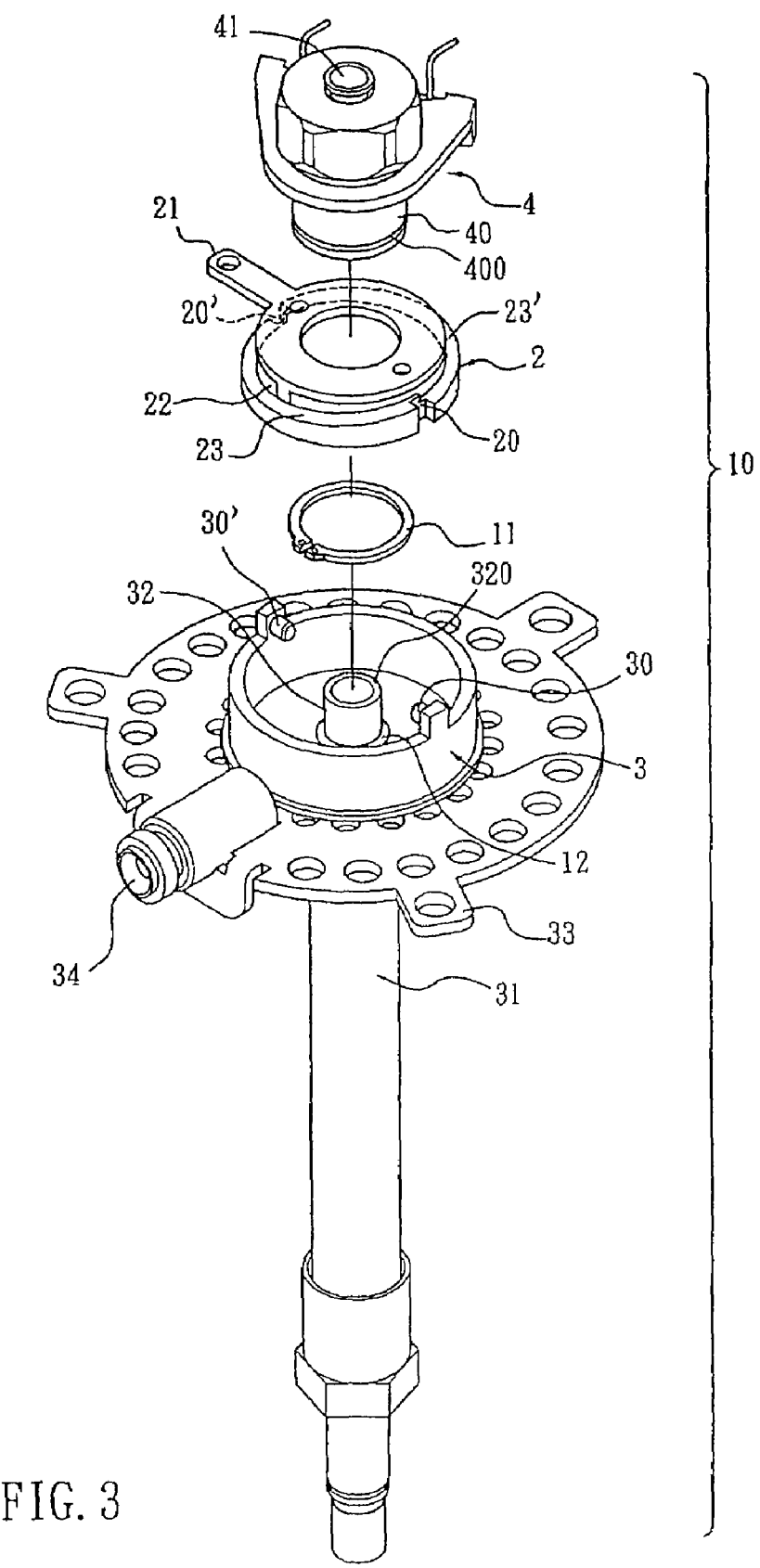
FIG. 3 illustrates an exploded view of the structure of the inlet of FIG. 2 in accordance with one embodiment of the present invention.

FIG. 3 is an exploded view of the structure of the inlet 10 of FIG. 2 in accordance with one embodiment of the present invention. The bottom assembly 3 includes one or more male units (e.g., 30 and 30'). In one embodiment, the bottom assembly 3 includes one male unit. In another embodiment, the bottom assembly 3 includes two male units 30 and 30' (as shown in FIG. 3). In a further embodiment, the bottom assembly 3 includes three or more male units. Each male unit can take various shapes. For example and as can be seen from FIG. 3, the male units 30 and 30' are two cylindrical pins. The male units 30 and 30' are 180° symmetrically attached to the annular wall of the bottom assembly 3. In one embodiment, the male units 30 and 30' can be assembled or soldered to the annular wall of the bottom assembly 3. In another embodiment, the male units 30 and 30' can be integrally formed with the annular wall of the bottom assembly 3.

In another embodiment, the bottom assembly 3 includes a shell unit 31 (as shown in FIG. 3). The shell unit 31 is arranged under the bottom assembly 3 so as to receive a liner 32 in which the sample is vaporized for analysis.

The top assembly 2 (a cam assembly as shown in FIG. 3) is of an annular shape and includes one or more female units (e.g., 20 and 20'). In one embodiment, the top assembly 2 includes one female unit. In another embodiment, the top assembly 2 includes two female units 20 and 20' (as shown in FIG. 3). In a further embodiment, the top assembly 2 includes three or more female units. The female unit can take various shapes. For example and as can be seen from FIG. 3, the female units 20 and 20' are two notches which are 180° symmetrically formed at both sides of the top assembly 2. The female units 20 and 20' can be of any shapes that can receive the male units 30 and 30'. In one embodiment, the female units 20 and 20' have inclined surfaces (i.e., reverse-dovetail-shaped notches) such that the male units 30 and 30' can be easily aligned with the female units 20 and 20'.

The top assembly 2 further includes one or more beveled surfaces (e.g., 23 and 23'). In one embodiment, the top assembly 2 includes one beveled surface. In another embodiment, the top assembly 2 includes two beveled surfaces 23 and 23' (as shown in FIG. 3). The relationship between the male units 30 and 30' and the beveled surfaces 23 and 23' will be further described below, also in conjunction with FIGS. 4a-4c.

The top assembly 2 further includes a lateral driving unit 21 for laterally driving the top assembly 2 to be sealed with the bottom assembly 3. Here, the term laterally means that the driving unit 21 causes the top assembly 2 to move laterally or horizontally with respect to the bottom assembly 3. The lateral driving unit 21 is arranged on a side of the top of a circular platform 22 of the top assembly 2. In one embodiment, the lateral driving unit 21 can be assembled or soldered to the side of the circular platform 22. In another embodiment, the lateral driving unit 21 can be integrally formed with the circular platform 22.

The lateral driving unit 21 can take various types. For example and as can be seen from FIG. 3, the lateral driving unit 21 is a handle. In another embodiment, the lateral driving unit 21 can be an opening or a pin on the top assembly 2 and is driven by an associated tool (such as a handle or a rod). In another embodiment, the lateral driving unit 21 can also be a driving unit which can laterally drive (or rotate) the top assembly 2, such as a pneumatic unit, power-driven unit, magnetic-driven unit or hydraulic unit.

Figure 4A:
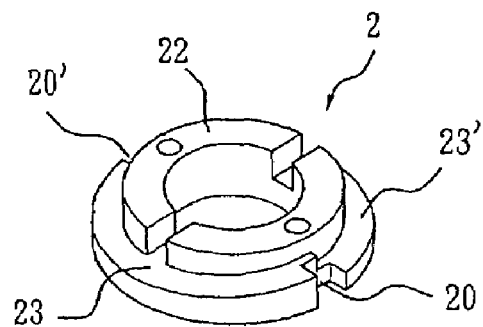
FIG. 4a illustrates a perspective view of the top assembly of the inlet of FIG. 2 in accordance with one embodiment of the present invention.
Figure 4C:
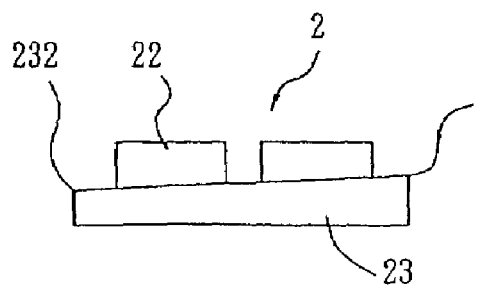
FIG. 4c illustrates the other side view of the top assembly of the inlet of FIG. 2 in accordance with one embodiment of the present invention.
Figure 4B:
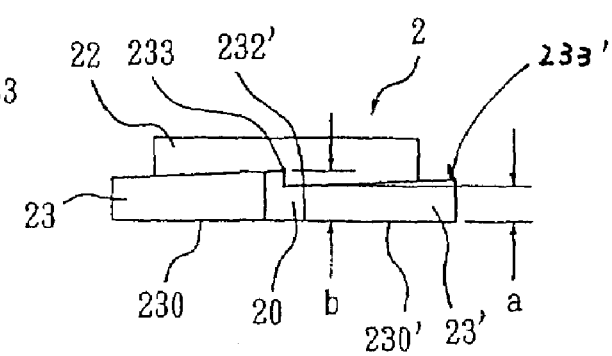
FIG. 4b illustrates a side view of the top assembly of the inlet of FIG. 2 in accordance with one embodiment of the present invention.

FIG. 4a illustrates a perspective view of the top assembly 2 of the inlet 10 of FIG. 2 in accordance with one embodiment of the present invention. FIGS. 4b and 4c illustrate different side views of the top assembly 2 of the inlet 10 of FIG. 2. As can be seen from FIGS. 4a, 4b, and 4c, a first beveled surface 23 and a second beveled surface 23' oppositely surround the circular platform 22. The two female units 20 and 20' are formed as two 180° symmetric notches between the first beveled surface 23 and the second beveled surface 23'. The bottom surfaces 230 and 230' of the first beveled surface 23 and the second beveled surface 23' are on the same plane. However, the surfaces of the first beveled surface 23 and the second beveled surface 23' are beveled in a half-circle spiral way and the gradients thereof are the same. The lowest position 232 (corresponding to the lowest height "a") and the highest position 233 (corresponding to the highest height "b") of the first beveled surface 23 are adjacent to the highest position 233' and the lowest position 232' of the second beveled surface 23', respectively.

For sealing the top assembly 2 with the bottom assembly 3 after a new liner 32 is replaced, the male units 30 and 30' of the bottom assembly 3 are first aligned with the female units 20 and 20' of the top assembly 2, respectively. After the top assembly 2 is aligned with the bottom assembly 3 and put into the bottom assembly 3, the lateral driving unit 21 drives the top assembly 2 laterally so as to rotate the top assembly 2.

Figure 5:
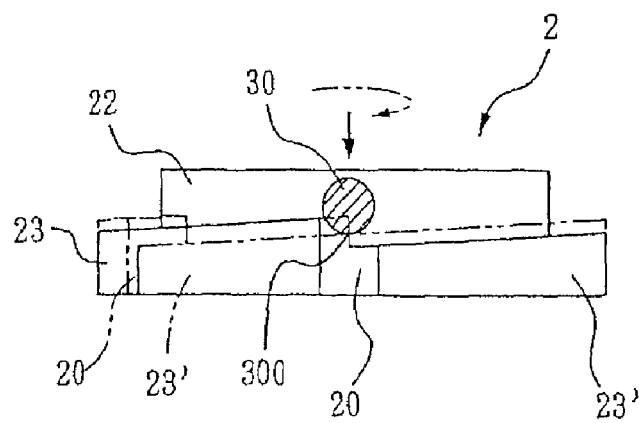
FIG. 5 illustrates a schematic diagram of the operation of the top assembly of the inlet of FIG. 2 in accordance with one embodiment of the present invention.

FIG. 5 illustrates a schematic diagram of the operation of the top assembly 2 of the inlet 10 of FIG. 2 in accordance with one embodiment of the present invention. When the top assembly 2 is rotated by the lateral driving unit 21 (rotated clockwise as shown in FIG. 5), the first beveled surface 23 and the second beveled surface 23' of the top assembly 2 rotate clockwise accordingly. Therefore, the heights of the first beveled surface 23 and the second beveled surface 23' of the top assembly 2 rise upwardly from the lowest positions 232 and 232' along the beveled surfaces 23 and 23', whereby the top assembly 2 gradually seals with the bottom assembly 3.

Because the lowest positions 300 and 300' (not shown) of the male units 30 and 30' of the bottom assembly 3 are higher than the lowest positions 232 and 232' of the beveled surfaces 23 and 23' of the top assembly 2 and are lower than the highest positions 233 and 233' of the beveled surfaces 23 and 23' of the top assembly 2, the top assembly 2 cannot be further rotated when the first beveled surface 23 and the second beveled surface 23' are at the height against the lowest positions 300 and 300' of the male units 30 and 30' of the bottom assembly 3, respectively (as shown by the phantom line in FIG. 5). Meanwhile, a sealing rubber O-ring 12 on the liner 32 is also pressed tightly. Thereafter, the top assembly 2 is sealed with the bottom assembly 3, thereby preventing the carrier gas and the vaporized sample from leaking out of the inlet 10.

In accordance with one embodiment of the present invention, the top assembly 2 and the bottom assembly 3 can easily be aligned and sealed together within at most half-circle rotation of the top assembly 2. Therefore, the liner replacement operation is both simple and user-friendly. Not only the time for liner replacement is saved, but also the damage to the top assembly 2, the bottom assembly 3, and the liner 32 is minimized.

Referring to FIG. 3 again, in accordance with another embodiment of the present invention, the bottom assembly 3 may further include a heat-dissipating plate 33. The heat-dissipating plate 33 is arranged between the bottom assembly 3 and the shell unit 31 for dissipating the heat generated.

In accordance with another embodiment of the present invention, the bottom assembly 3 may further include a splitter 34 for pushing a pre-set portion of concentrated sample to the vent and out of the inlet 10. Therefore, a large amount of the sample is prevented from entering and saturating in a column and a detector of a gas chromatograph system to which the inlet 10 is applied.

In accordance with another embodiment of the present invention, the gas flow unit 4 is used for providing carrier gas for analysis and purge gas to purge back-flushed sample, and any bleed-off gas from septum 41 or O-ring 12 out of the internal space of the top assembly 2. The gas flow unit 4 may further include a septum 41 and a tubular lower portion 40. The tubular lower portion 40 penetrates the top assembly 2 and is fastened to the top assembly 2 with a C-ring 11 surrounding a slot 400 on the tubular lower portion 40. Therefore, a needle in injector (not shown) can punch through the septum 41 downwardly to inject the sample to be analyzed into the liner 32. In addition, when the top assembly 2 is sealed with the bottom assembly 3, the tubular lower portion 40 further covers the top portion 320 of the liner 32 to prevent the carrier gas and the vaporized sample from leaking out of the inlet 10.

Figure 6:
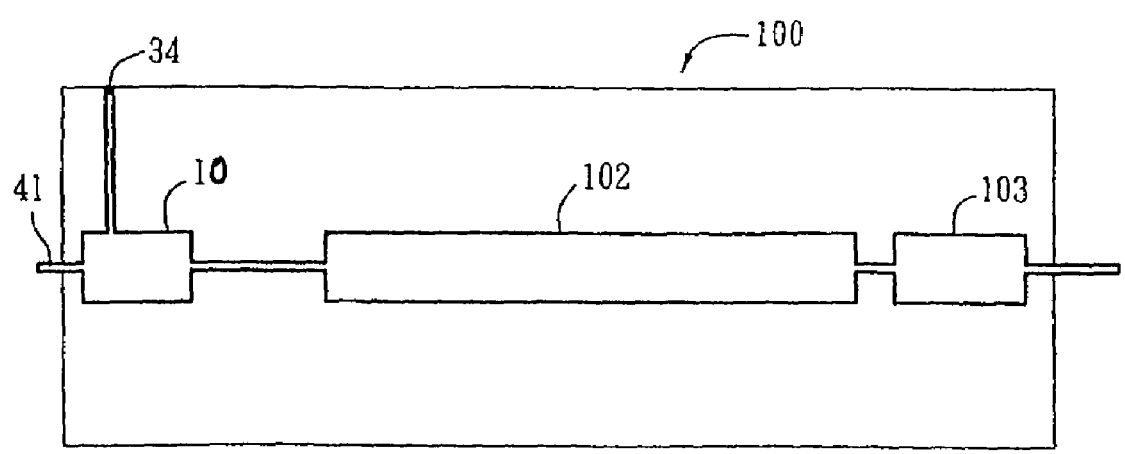
FIG. 6 is a schematic diagram of a gas chromatograph system that employs the inlet of FIG. 2 in accordance with one embodiment of the present invention.

FIG. 6 is a schematic diagram of a gas chromatograph system 100 that includes the inlet 10 of FIG. 2 in accordance with one embodiment of the present invention. The gas chromatograph system 100 further includes a column 102 and a detector 103. The inlet 10 is used for injecting the sample to be analyzed. The column 102 is connected to the inlet 10 for receiving and separating the sample to be analyzed from the inlet 10. The detector 103 is connected to the column 102 and detects the compounds of the separated sample to be analyzed from the column 102.

The foregoing discussion discloses and describes merely exemplary methods and embodiments of the present invention. As will be understood by those familiar with the art, the invention may be embodied in other specific forms without departing from the spirit or essential characteristics thereof. Accordingly, the disclosure of embodiments of the present invention is intended to be illustrative, but not limiting.

What is claimed is:

1. A gas chromatograph system, comprising:
    an inlet that further comprises
        a bottom assembly including at least one male unit; and
        a top assembly having at least one beveled surface, further including
            at least one female unit; and
            a lateral driving unit placed on the top assembly, wherein when the top assembly is placed inside the bottom assembly by aligning the female unit of the top assembly with the male unit of the bottom assembly, and when the lateral driving unit laterally drives the top assembly, the beveled surface of the top assembly rises against the male unit of the bottom assembly, allowing the top assembly to seal with the bottom assembly.

2. The gas chromatograph system of claim 1, wherein the male unit is a cylindrical pin and the female unit is a notch.

3. The gas chromatograph system of claim 1, wherein the bottom assembly further comprises a second male unit and the top assembly further comprises a second female unit.

4. The gas chromatograph system of claim 3, wherein the top assembly is of an annular shape and further comprises a second beveled surface, wherein the first female unit and the second female unit are 180° symmetrically formed between the first beveled surface and the second beveled surface.

5. The gas chromatograph system of claim 1, wherein the female unit is a reverse-dovetail-shaped notch.

6. The gas chromatograph system of claim 1, further comprising a second beveled surface, a second male unit and a second female unit,
    wherein when the top assembly is placed inside the bottom assembly by simultaneously aligning the second female unit of the top assembly with the second male unit of the bottom assembly, and when the lateral driving unit laterally drives the top assembly, the second beveled surface of the top assembly simultaneously rises against the second male unit of the bottom assembly, allowing the top assembly to seal with the bottom assembly.

7. The gas chromatograph system of claim 3, wherein bottom assembly comprises an annular wall and the first and second male units are 180°symmetrically attached to the annular wall of the bottom assembly.

8. The gas chromatograph system of claim 1, wherein when the top and bottom assemblies are sealed, the position of the first male unit is higher than the lowest position of the first beveled surface of the top assembly and is lower than the highest position of the first beveled surface of the top assembly.

9. The gas chromatograph system of claim 1, wherein the lateral driving unit is a unit selected from a handle, a pneumatic unit, a power-driven unit, a magnetic-driven unit or a hydraulic unit.

10. The gas chromatograph system of claim 1, wherein the top assembly is a cam assembly.

* * * * *